(12) United States Patent
Maistri et al.

(10) Patent No.: US 10,187,433 B2
(45) Date of Patent: Jan. 22, 2019

(54) METHODS AND SYSTEMS FOR DYNAMIC ADJUSTMENT OF SESSION PARAMETERS FOR EFFECTIVE VIDEO COLLABORATION AMONG HETEROGENOUS DEVICES

(71) Applicant: SwyMe IP BV, Noordwijk (NL)

(72) Inventors: Paolo Maistri, Verona (IT); Stefano Migliorisi, Washington, DC (US); Giannantonio Costermani, Verona (IT); Jeffrey Samuel Urdan, Lexington, MA (US)

(73) Assignee: SWYME IP BV, Noordwijk (NL)

( * ) Notice: Subject to any disclaimer, the term of this patent is extended or adjusted under 35 U.S.C. 154(b) by 0 days.

(21) Appl. No.: 15/583,710

(22) Filed: May 1, 2017

(65) Prior Publication Data
US 2017/0237784 A1 Aug. 17, 2017

Related U.S. Application Data

(63) Continuation-in-part of application No. 14/774,077, filed as application No. PCT/US2014/031065 on Mar. 18, 2014, now Pat. No. 9,641,559.
(Continued)

(51) Int. Cl.
| | |
|---|---|
| *H04N 7/14* | (2006.01) |
| *H04L 29/06* | (2006.01) |
| *H04L 12/24* | (2006.01) |
| *H04W 28/02* | (2009.01) |
| *H04L 12/803* | (2013.01) |
| *H04N 7/15* | (2006.01) |

(Continued)

(52) U.S. Cl.
CPC ........ *H04L 65/1083* (2013.01); *H04L 41/147* (2013.01); *H04L 47/125* (2013.01); *H04L 65/1069* (2013.01); *H04L 65/403* (2013.01); *H04L 69/14* (2013.01); *H04N 7/148* (2013.01); *H04N 7/152* (2013.01); *H04W 28/02* (2013.01); *G06Q 10/101* (2013.01); *G16H 80/00* (2018.01); *H04L 67/12* (2013.01)

(58) Field of Classification Search
USPC .............................. 348/14.02, 14.08, 14.12
See application file for complete search history.

(56) References Cited

U.S. PATENT DOCUMENTS

| | | | |
|---|---|---|---|
| 6,128,649 | A | 10/2000 | Smith et al. |
| 6,833,863 | B1 | 12/2004 | Clemens |
| 7,600,012 | B2 | 10/2009 | Burg et al. |
| 7,773,581 | B2 | 8/2010 | Punj et al. |

(Continued)

OTHER PUBLICATIONS

International Search Report of related International Patent Application No. PCT/US2014/031065 dated Aug. 27, 2014.

*Primary Examiner* — Quoc D Tran
(74) *Attorney, Agent, or Firm* — Arent Fox LLP

(57) ABSTRACT

Methods and systems for mobile video communications may include using a wireless network for video communications when a wired network is unavailable by providing portable mobile communications equipment to enable video communications and collaborations over a cellular, satellite or other wireless network. The methods and systems may use two or more network connections to transmit data packets for the video communications or collaborations. In addition, the methods and systems may use machine learning and predictive switching technology to determine the data paths for transmission of the data for the video communications or collaborations.

18 Claims, 17 Drawing Sheets

Related U.S. Application Data

(60) Provisional application No. 61/799,269, filed on Mar. 15, 2013.

(51) Int. Cl.
    *H04L 29/08*     (2006.01)
    *G06Q 10/10*     (2012.01)
    *G16H 80/00*     (2018.01)

(56) References Cited

U.S. PATENT DOCUMENTS

| Patent/Publication No. | Date | Inventor | Classification |
|---|---|---|---|
| 8,144,187 B2 | 3/2012 | Moore et al. | |
| 8,194,114 B2 | 6/2012 | Barry et al. | |
| 8,665,313 B2 | 3/2014 | Li et al. | |
| 9,641,559 B2* | 5/2017 | Maistri | H04L 65/1069 |
| 2003/0023672 A1 | 1/2003 | Vaysman | |
| 2003/0208541 A1 | 11/2003 | Musa | |
| 2004/0034723 A1 | 2/2004 | Giroti | |
| 2004/0131061 A1* | 7/2004 | Matsuoka | H04W 8/14 370/392 |
| 2004/0179591 A1 | 9/2004 | Wenger et al. | |
| 2008/0024593 A1 | 1/2008 | Tsirinsky et al. | |
| 2009/0225670 A1 | 9/2009 | Leung et al. | |
| 2009/0315975 A1 | 12/2009 | Wiener et al. | |
| 2011/0077001 A1* | 3/2011 | Brown | H04W 24/00 455/426.1 |
| 2011/0096673 A1 | 4/2011 | Stevenson et al. | |
| 2011/0157298 A1 | 6/2011 | Huang et al. | |
| 2011/0249077 A1 | 10/2011 | Abuan et al. | |
| 2011/0283203 A1 | 11/2011 | Periyannan et al. | |
| 2013/0077486 A1 | 3/2013 | Keith | |
| 2013/0078978 A1* | 3/2013 | Booth | H04W 8/20 455/418 |

\* cited by examiner

Data Packets

| 0 | 1 | 2 | 3 | 4 | 5 | 6 | 7 | 8 | 9 | 10 | 11 |
|---|---|---|---|---|---|---|---|---|---|----|----|
| ID | Size | | Time code | | | | Profile | Channel | | Subchannel | Streaming data |

Fig. 8

Atomic Streaming Packets

| 0 | 1 | 2 | 3 | 4 | 5 | 6 | 7 | 8 | 9 | 10 | 11 | 12 |
|---|---|---|---|---|---|---|---|---|---|----|----|----|
| ID | Size | | Source Peer ID | | | | Session ID | Sequence Number | | | | Streaming packet |

Non-atomic Streaming Packets

| 0 | 1 | 2 | 3 | 4 | 5 | 6 | 7 | 8 | 9 | 10 | 11 | 12 | 13 | 14 | 15 | 16 |
|---|---|---|---|---|---|---|---|---|---|----|----|----|----|----|----|----|
| ID | Size | | Source Peer ID | | | | Session ID | Sequence Number | | | | Blocks count | | Blocks index | | Streaming packet portion |

Fig. 9

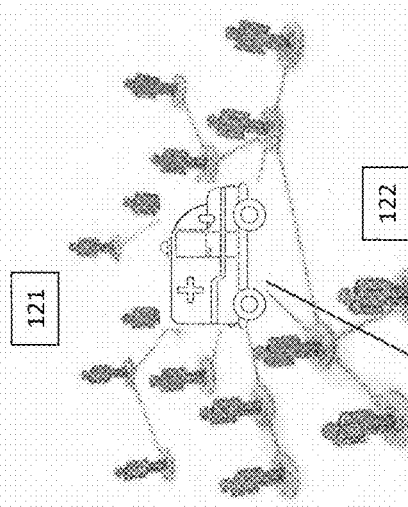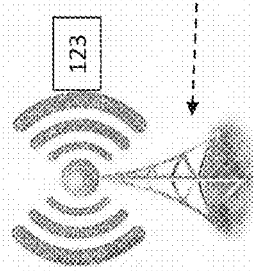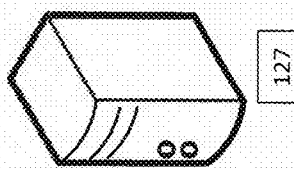
Fig. 12

141 Ruggedized Tablet

METHODS AND SYSTEMS FOR DYNAMIC ADJUSTMENT OF SESSION PARAMETERS FOR EFFECTIVE VIDEO COLLABORATION AMONG HETEROGENOUS DEVICES

RELATED APPLICATIONS

This application is a Continuation-in-part of U.S. patent application Ser. No. 14/774,077, filed Sep. 9, 2015, which is a National Stage Entry of International Patent Application No. PCT/US14/31065, filed Mar. 18, 2014, which claims priority to U.S. Application No. 61/799,269 titled "Methods and Apparatuses for Dynamic Adjustment of Session Parameters for Effective Video Collaboration Among Heterogeneous Devices," filed Mar. 15, 2013. The disclosures of the priority applications are incorporated herein by reference in their entirety.

BACKGROUND OF THE INVENTION

Video conferencing and collaboration are used by a limited number of businesses worldwide due to its high costs, dedicated hardware, heavy use of bandwidth, and complexity.

While video conferencing devices are typically based on the H.323 standard to ensure interoperability, devices made by different manufacturers are still not always able to "talk" to each other during a video conference or other collaboration session.

The advent of the Internet, but especially the increase of available bandwidth on the network, combined with the increase in computational capabilities of computers and mobile devices, has allowed the creation of software capable of video communication, using "low-cost" devices compared to the H.323 systems. These software programs have allowed video conferencing to spread to a much wider audience and, more importantly, heterogeneous devices. There are a great number of hardware devices that can be turned into a "video device," able to encode audio and video locally and decode/play back audio and videos received from remote locations.

Thus, there are now two worlds: those with low cost/low quality software-based solutions, and those with high cost/high quality hardware based solutions. These two worlds are usually isolated, as companies often purchase software only solutions for employee desktops, and high quality solutions for executive meetings/conference rooms.

There remains an unmet need for a single software solution that may cover both requirements, i.e., offer "low cost" and "high quality" at a much lower cost than hardware solutions, allowing users to connect from any device to the same meeting.

To accomplish this, the software needs to ensure that each participant enjoys the best possible quality based on the capabilities available to the participants, such as the hardware devices in use and/or the type and quality of the network link.

In addition, traditional video conferencing applications require high bandwidth connections which limit the mobility of participants. The bandwidth available and network irregularities (e.g., latency and jitter) in cellular, satellite and other wireless data networks make traditional solutions unsuitable or usable only in very limited areas.

Thus, there remains a need in the art for improvements in the mobility of video conferences and collaboration sessions.

SUMMARY

Aspects of the present invention relate to methods and systems to maximize the quality perceived by the user in a software-based, multi-point video conference or collaboration session between devices that are potentially different (e.g., devices from different vendors, devices with different operating systems, devices on different networks, devices that function as servers, clients or both) and maintain the quality over time.

The methods and systems may, for example, determine an optimal initial configuration for each device involved in the videoconference based on the session parameters, hardware characteristics of the devices and the characteristics of the network used. During the videoconference, a videoconferencing platform may modify the initial configuration to adapt to changes that may occur related to the performance of the session, such as the arrival of a new participant, enabling sharing of documents, and/or changes in network bandwidth and/or modification of the hardware configuration of the device used, such as the addition/removal of "plug and play" devices. The changes mentioned are only for illustrative purposes and do not cover the entire range of changes that may happen during the course of a videoconference. It is well known to those skilled in this field that there are numerous factors that may impact the perceived quality of the interaction, most of them beyond the control of videoconferencing application software.

The changes may include, for example, bit rate and/or settings for capturing video (frame rate/frame size/color space/device) in the transmissions and/or changing the type of streams received. These changes may affect one or more devices involved in the videoconference, as the devices may be treated by the platform as independent, with their own characteristics, and the interaction of multiple devices may not be treated as a single call with a uniform application of settings across devices.

The methods and systems may also use a cellular, satellite or other wireless networks for communications when a wired network is unavailable by providing portable mobile communications equipment to enable video collaboration. The methods and systems may use two or more network connections to transmit data packets for the video collaboration. In addition, the methods and systems may use machine learning and predictive switching technology to determine the best data path for transmission of the data for the video collaboration.

Additional advantages and novel features relating to aspects of the present invention will be set forth in part in the description that follows, and in part will become more apparent to those skilled in the art upon examination of the following or upon learning by practice thereof.

DESCRIPTION OF THE FIGURES

In the drawings:

FIG. 8 illustrates an example data packet in accordance with an aspect of the present invention;

FIG. 9 illustrates example atomic streaming packets and non-atomic streaming packets in accordance with an aspect of the present invention;

FIG. 12 illustrates the challenge of data loss over cellular data networks in accordance with an aspect of the present invention;

DETAILED DESCRIPTION

Figure 1:
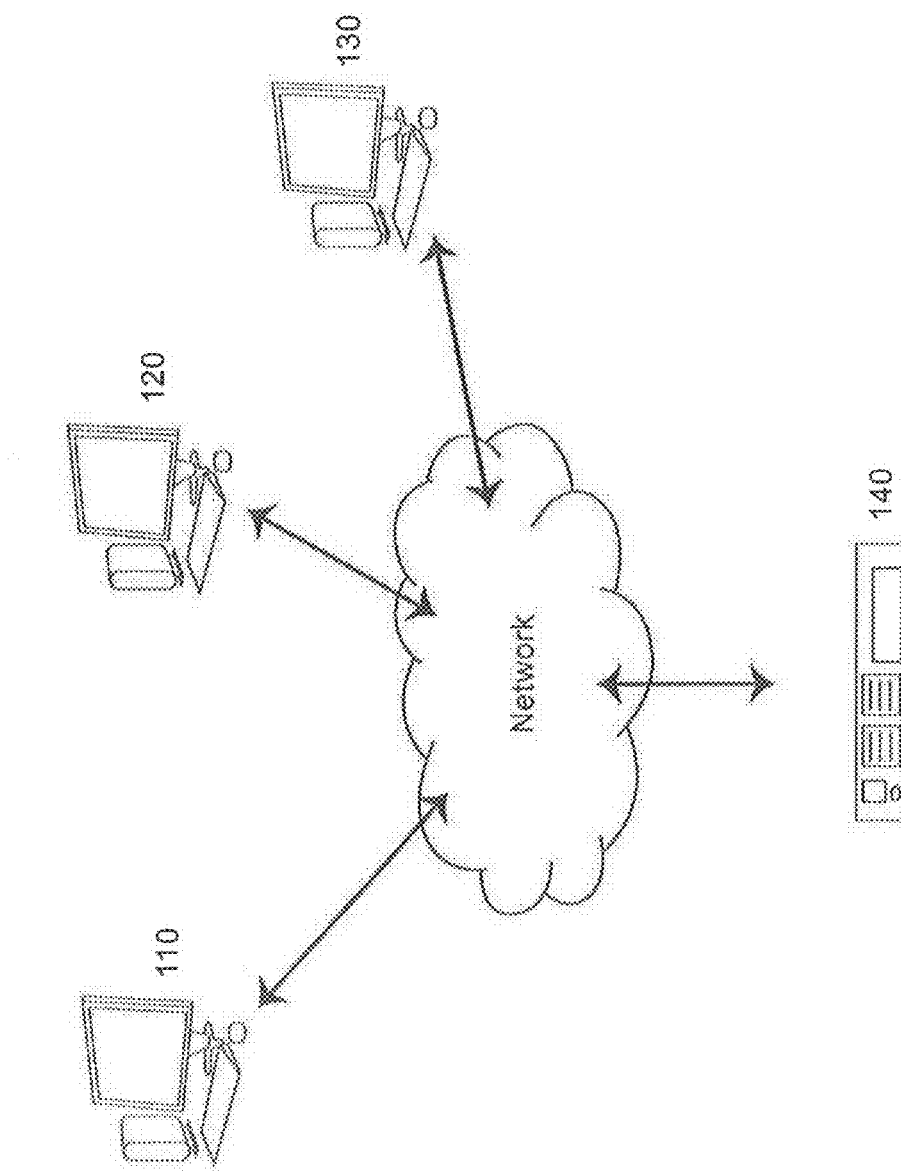
FIG. 1 illustrates videoconferencing communication devices connected to the video server in accordance with an aspect of the present invention.

Aspects of the present invention relate to methods and systems for maximizing the quality perceived by the user and maintaining quality at the best possible level for most of the duration of a multipoint videoconference and/or other information exchange conducted among different devices (e.g., computers, tablets, smart phones, wearable streaming devices, remote monitoring stations). Devices may include, for example, any electronic suitable device capable of executing a software program, whether a mobile device or not, capable of capturing/playing video and audio content as well as displaying shared desktops. Devices may function as servers, clients or both at the same time. In addition, the term computer or computer system used throughout the document may refer to a computing device that can be turned into a "video device," for example, a computing device that has hardware capabilities to encode audio and video locally and decode/play back audio and videos received from remote locations. Throughout this document, references are made to "videoconference(s)"; however, videoconference(s) should be interpreted to include a wider variety of collaboration including, but not limited to, file sharing, desktop sharing and mark-up, shared whiteboard, text chat, audio and video conferencing.

The methods and systems may determine an optimal initial configuration for each device involved in the videoconference, for example, based on the session parameters, hardware characteristics of the devices, and the characteristics of the network used. During the videoconference, a videoconferencing platform may modify the initial configuration to adapt to changes that may occur, related to the performance of the session, such as the entrance of a new participant, sharing of documents, and/or changes in network bandwidth and/or modification of the hardware configuration of the device used, such as, for example, the addition/removal of plug-n-play devices.

The changes to session parameters may include bit rate and/or settings for capturing video ahead of transmission and/or changing the type of streams received. These changes may affect one or more devices involved in the videoconference, as the devices may be independent from each other and with their own characteristics.

By having the flexibility to allow participants to connect to a video conference from a variety of platforms and/or devices, participants may join the video conference from any location and/or at any time. Moreover, with the ability to connect to the video conference from a mobile device, participants have the ability to take the video conference with them as the participant moves and/or changes locations.

The described aspects may provide participants with a high quality, high-definition (HD) video and audio conferencing, chat functionality, and application sharing, for example. The video conferencing system may allow participants to collaborate through application sharing, desktop sharing, testing and/or polling, file transfers, integrated whiteboards, document sharing and/or integrated flip charts. For example, participants may collaborate by contributing to a document displayed concurrently with the video conference by providing edits, comments, and/or images to the same document. In addition, the video conferencing system may allow participants to chat (e.g., transmit messages to each other) concurrently with the video conference occurring. Participants may have side conversations with each other using the chat function without disrupting the current speaker on the call and/or having other participants on the call view the side conversation.

The described aspects may also allow participants to record the video conference so that participants who are unable to attend the video conference may view the video conference at a later time. In addition, the described aspects may allow participants to be added to the video conference with ease, for example, by sending an e-mail to the participant with a link to the video conference.

The described aspects may use the below discussed session protocol in transmitting the streaming data packets for the video conferencing system and managing the transport of audio, video, and application sharing data. These data packets may have a size ranging from a few tens of bytes to one hundred kilobytes. In addition, the session protocol may optimize data transmission over land and satellite (high latency, frequent packet loss) networks.

In addition, the described aspects may use a cellular or other wireless networks for video communications and/or collaborations when a wired network is unavailable. The methods and systems may provide mobile communications equipment to enable video communications (e.g., a videoconference call) and/or collaborations (e.g., data, image and other non-video sharing). The mobile communications equipment may be portable and include a resilient network architecture and machine learning to enable predictive network switching to optimize the user experience. In an aspect, the methods and systems may use two or more network connections to transmit data packets for the video communications and/or collaborations. In addition, the methods and systems may use machine learning and predictive switching technology to determine the data paths for transmission of the data for the video communications and/or collaborations.

FIG. 8 illustrates an example data packet transmission in accordance with an aspect of the present invention where: ID is one BYTE (8-bit unsigned integer) defining the type of streaming packet being transported (i.e., audio, video, app sharing, or control), Size is a WORD (16-bit Unsigned Integer) indicating the overall size (in bytes) of the streaming packet, Time code is a DWORD (32-bit Unsigned Integer) providing the time stamp associated with the packet, Profile is a BYTE identifying the profile used for the encoding of streaming data, Channel is a WORD identifying the data channel associated to the streaming coming from a specific participant, Subchannel is a BYTE identifying a specific version of data streaming on the given channel, and Streaming data are the real streaming data (audio samples, video frames, etc.).

By inserting the WORD channel into the session protocol for transmitting the streaming data, different versions of the same content may be inserted into the streaming data and/or may be associated to a specific data stream. For example, various streaming data from the same source may be available for the video conference, such as low, medium, and/or high quality streams. The subchannel field may allow the video conferencing system to recognize the different versions of the same content identified by the channel field (e.g., low, medium, and/or high quality streams). In addition, the streaming data may have contemporaneous translations of the audio corresponding to the video (e.g., an audio stream with the original voice data and/or different audio streams for each translator). The subchannel may identify the audio stream of each translator so a participant may select the audio stream in his/her preferred language.

In an aspect, participants in the video conference may have the option to select the best possible audio and video streaming data based upon, for example, a preferred language, processing power of a device and/or available bandwidth for the video conference. For example, the participant may use the subchannel to select the best possible audio and video stream for the video conference.

In another aspect, the device the participant is using to connect to the video conference may automatically select the best subchannel to stream the video conference, given parameters applicable to the device (e.g., processing power, available bandwidth, default language). For example, if the participant is using a mobile device in an area of coverage with a lower amount of available bandwidth, the mobile device may automatically select a lower quality subchannel of the video conference to stream. However, if the participant moves to an area of coverage with a higher area of coverage and/or more bandwidth available, the mobile device may automatically switch to a higher quality subchannel of the video conference to stream.

Another aspect may include threshold driven streaming. For example, the video conferencing system may adjust the streaming parameters automatically and/or dynamically when one or more parameters that influence quality of the video conference exceed a threshold value. An alert, such as a notification message, changing color and/or fonts on a display, and/or an audio signal (e.g., a beep, an alarm, a voice notification) may be generated and sent when one or more parameters (e.g., Round Trip Time (RTT), Jitter, Packet loss, central processing unit (CPU) usage) exceed a threshold value that defines a minimum acceptable quality. For example, an alert may be generated notifying the video conferencing system that the jitter exceeds the jitter threshold value. Upon receiving an alert, the video conferencing system may adjust the one or more parameters that exceed the threshold value, accordingly, by changing, for example, the subchannel of the streaming data and/or modifying the upload transmission.

For example, if the upload bandwidth is suddenly reduced and the RTT exceeds a RTT threshold value, an alert may be generated notifying the video conferencing system that the RTT threshold value has been exceeded. Upon receiving the alert, the video conferencing system may change one or more parameters affecting the upload bandwidth, such as frame size, frame rate, or other encoder settings) to reduce the bandwidth usage. By reducing the bandwidth usage, the session may continue with a reduced but acceptable quality (e.g., without interruptions). When the alert stops (e.g., the bandwidth is increased and the RTT moves below the RTT threshold value), the video conferencing system may reset the parameters to the original values and return the video conference quality back to the original level.

In an aspect, the transport of streaming data may be carried out by using atomic streaming packets (whose size does not exceed a network threshold value), as well as by using non-atomic streaming packets (whose size does exceed the network threshold value). These packets may have a size ranging from a few tens of bytes to one hundred kilobytes. To optimize the data transmission, the size of each packet may be set so as not to exceed a certain network value (e.g., about one thousand bytes). The transport of streaming data may be carried out, for example, according to the structure illustrated in FIG. 9, where ID is a BYTE that defines the type of packet being transported (atomic/non-atomic), Size is a WORD that defines the overall size (in bytes) of the packet being sent, Source Peer ID is a DWORD including the sender ID, Session ID is a BYTE defining the session associated to the stream, Sequence number is a DWORD indicating the progressive number of the packet within a broadcast sequence, Blocks count is WORD indicating how many packets are necessary to reconstruct the entire streaming packet, Block index is a WORD indicating the position of the packet within the packet sequence of which the packet forms part, and Streaming packet portion is either the full packet or a portion in the case of non-atomic streaming packets.

By using atomic and non-atomic packets and socket buffering, for example, the quality of the video conference may be increased when the download bandwidth is constrained and/or the upload bandwidth is suddenly reduced.

In another aspect, the video conferencing system may allow asynchronous data exchange to occur that is enabled by a proprietary library placed on the operating system platform. The asynchronous data exchange enabled by such library may free the application layer from issues caused by Transmission Control Protocol (TCP) (e.g., delays in data transmission due to management and recovery of data packets lost over the network) that makes the use of TCP in real time communications inferior to User Datagram Protocol (UDP) (the standard transport protocol of software and hardware based videoconferencing). Thus, by using the library for asynchronous data exchange, the video conferencing system may maintain the advantages of using TCP, such as automatic packet recovery and "built-in" firewall and proxy traversal without the pitfalls of TCP (e.g., delays in data transmission due to management and recovery of data packets lost over the network).

In the system architecture, described in FIG. 1, each video conferencing workstation (device) is connected to the server via a videoconference network (wired, wireless or mobile—for example, but not only, 3G, 4G, WiMAX).

Figure 2:
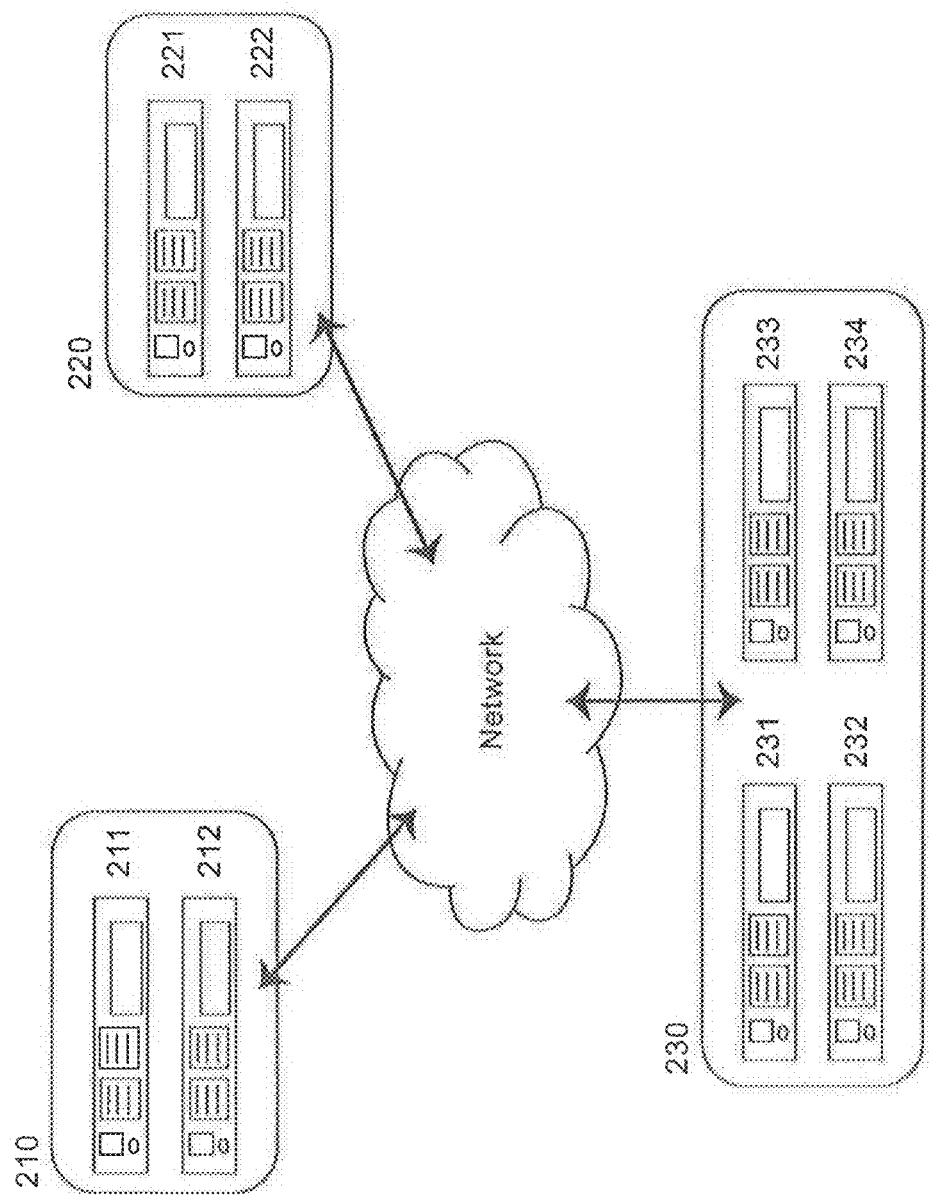
FIG. 2 illustrates general architecture of the server videoconferencing in accordance with an aspect of the present invention.

The term "videoconferencing server," as shown in FIG. 2, is not limited to a single server accessible by the devices, but may be extended to a cluster comprising one or more groups of servers (210, 220, 230) geographically dispersed and interconnected through high speed connections, where each group of servers includes one or more servers (211, 212, 221, 222, 231, 232, 233, 234) over a local network with load-balancing among them. In an aspect, the servers may be or include one or more relay servers.

Servers may include, for example, any physical electronic device (e.g., rack-mounted personal computer (PC), blade PC, desktop PC, laptop PC, mobile device) or virtual machine that can run the videoconferencing management platform and participate in a videoconferencing session. Any server can function both as server and device at the same time.

In an aspect, the load-balancing and fault tolerance among servers may be managed directly by the videoconferencing management platform through active communications among servers. For example, each server may know the state and the workload of the other servers, and may determine which server has the lowest workload and which server(s) may have an error (e.g., the server is not functioning properly).

This approach may provide cost savings, as there may be no need or reduced need to use a dedicated load-balancing cluster or external systems, including costs being further lowered when using virtual machines.

One or more video devices may connect to the server with the lowest workload within each group of relay servers. In an aspect, the group of relay servers to connect to may be determined based on the lowest latency of interconnection with a server and not necessarily the nearest physical/geographical connection to a server.

Figure 3:
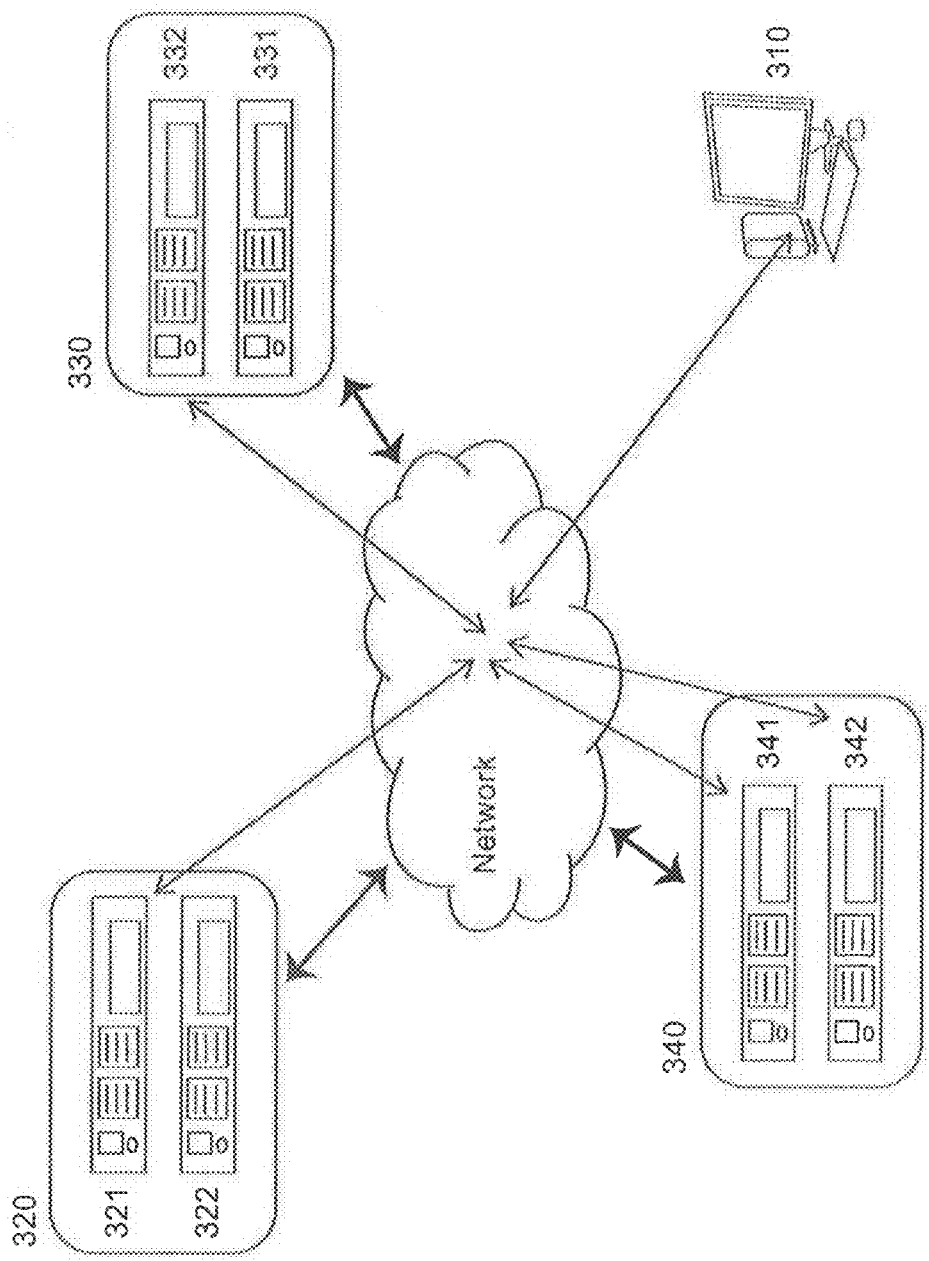
FIG. 3 illustrates a process of connecting a device to the server in accordance with an aspect of the present invention.

FIG. 3 illustrates a process that leads to connecting a device 310 with server 332. Device 310 may connect to any suitable server in a list of available servers (i.e., 321, 322, 331, 332, 341, or 342), receiving in response a list format including one active server for each group of relay servers (i.e., 320, 330, and 340). Device 310 may perform a latency test with each of the servers 321, 331, and 341, which may result in identifying, for example, the group of relay servers guaranteeing the minimum latency value. For example, the group of relay servers 340 may guarantee the minimum latency value and device 310 may connect with sever 341. In an aspect, server 341 may redirect device 310 to another server within the group of relay servers based on a determination of which server has the lowest workload in the group of relay servers. For example, server 341 may determine that server 342 has the lowest workload of each of the servers within the group of relay servers 340 and server 341 may redirect device 310 to server 342 based on the determination.

Each device may be placed behind a firewall and/or proxy without affecting the ability to conduct video conferences with other users, wherever they are. The traversal of firewalls and/or proxies and/or Network Address Translations (NATs) may occur without requiring any re-configuration, as data flows are made to pass through open Hypertext Transfer Protocol (HTTP)/Hypertext Transfer Protocol Secure (HTTPS) ports, and TCP/Internet Protocol (IP) is used for data transport.

Since TCP/IP was created to ensure lossless transmission of data, to avoid possible delays introduced by the retransmission of lost packets, aspects may include a multi-platform library that implements asynchronous TCP/IP sockets, whereby data transmission is not blocked waiting for any retransmission in order to ensure a low latency and thus maintains the synchronous reception of audio and video. In addition, these sockets may allow the streaming of such data to be less affected by fluctuations of the available upload bandwidth. A further optimization of data transmission may include sending packets with a maximum size no larger than a thousand bytes, for example, as packets that are larger may be fragmented into smaller ones and then reassembled at reception. This approach allows interspersed flows linked to the different channels (e.g., audio, video, data) to be transmitted in an optimized fashion using a single socket between each device and server.

If the network allows it, data may also be sent alternatively via UDP UNICAST or MULTICAST, and UNICAST and MULTICAST streams may be used in the same videoconferencing session. The system may detect, for each device, for example, which type of protocol to use based on the type of network between each device and server. The system may also support streaming of data via satellite networks.

One or more or each device may include a physical device (e.g., desktop PC, laptop PC, tablet, smart phone) able to run the conferencing platform (the program), directly or through devices to capture and play back audio (e.g., microphones and speakers, headset or Universal Serial Bus (USB) analog, external speakers, microphones, table microphones), as well as devices to capture video (e.g., integrated cameras, webcams, external HD or standard definition (SD) analog cameras combined with video capture cards, network cameras), or devices to view or render the videos and collaborative features (e.g., integrated monitor, one or more external monitors, projectors, high-definition television (HDTVs)).

It is obvious to those skilled in the field of audio/video that it is not possible to list all the possible solutions that the market offers to encode an audio/video signal, or to reproduce such signals from a computing device. Any suitable device that is able to encode an audio/video signal and decode the audio/video signal(s) received may be used for a video conferencing device.

This approach allows both a low-cost device for a single user and a high definition device for a conference room, to both be managed by the same program, for example.

Figure 4:
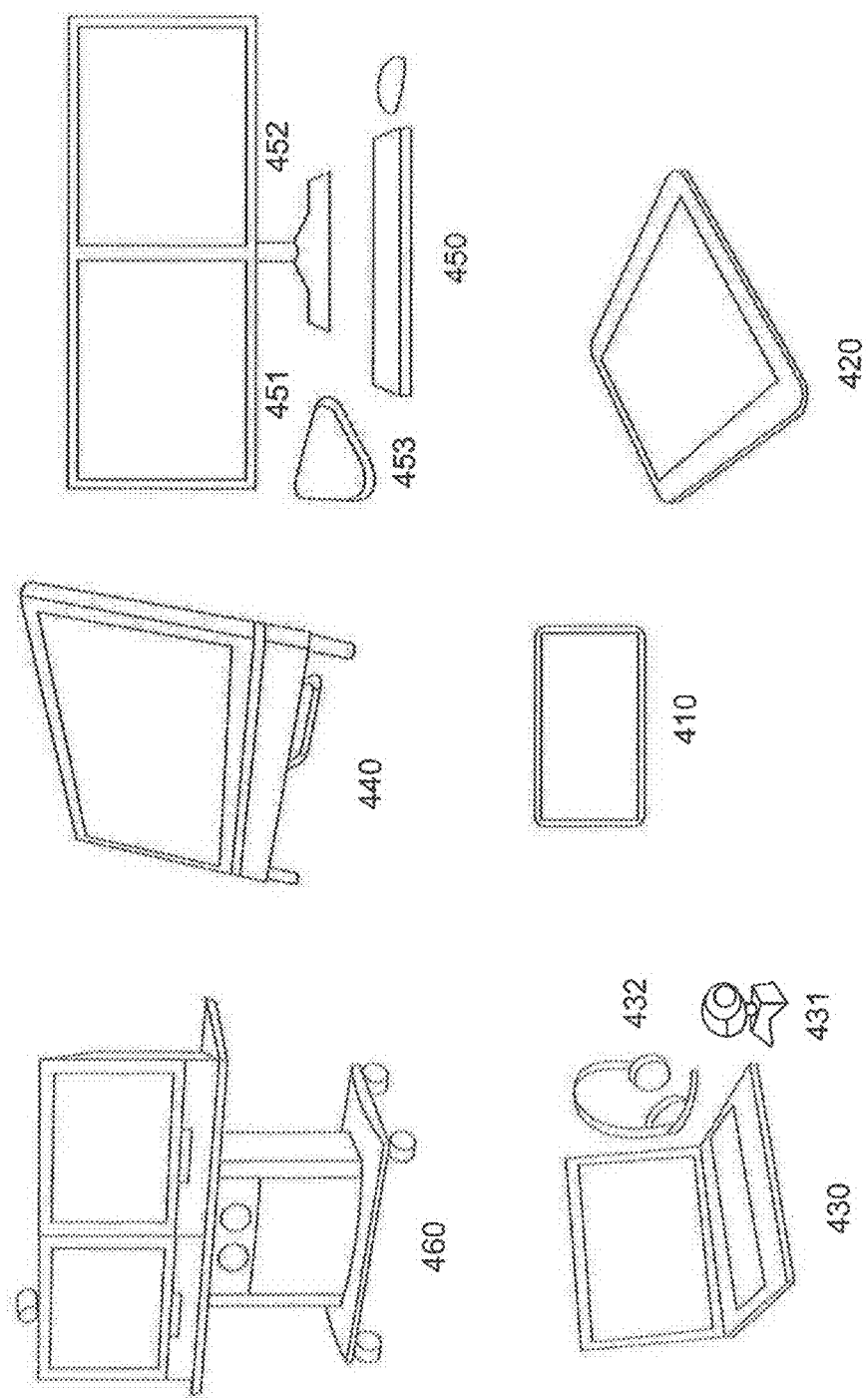
FIG. 4 illustrates examples of videoconferencing devices in accordance with an aspect of the present invention.

FIG. 4 illustrates some examples of devices usable in accordance with aspects of the present invention (410—smartphone, 420—tablet, 430—laptop with 431—webcam and 432—headset, 440—all-in-one PC, 450—desktop PC with dual monitors 451 and 452 and desktop microphone—453, meeting room system—460).

Each user may initiate a videoconference from his/her device, inviting one or more users contemporaneously, even when such devices have very different characteristics. For example, some devices may have high quality and other devices may have low quality.

Figure 5:
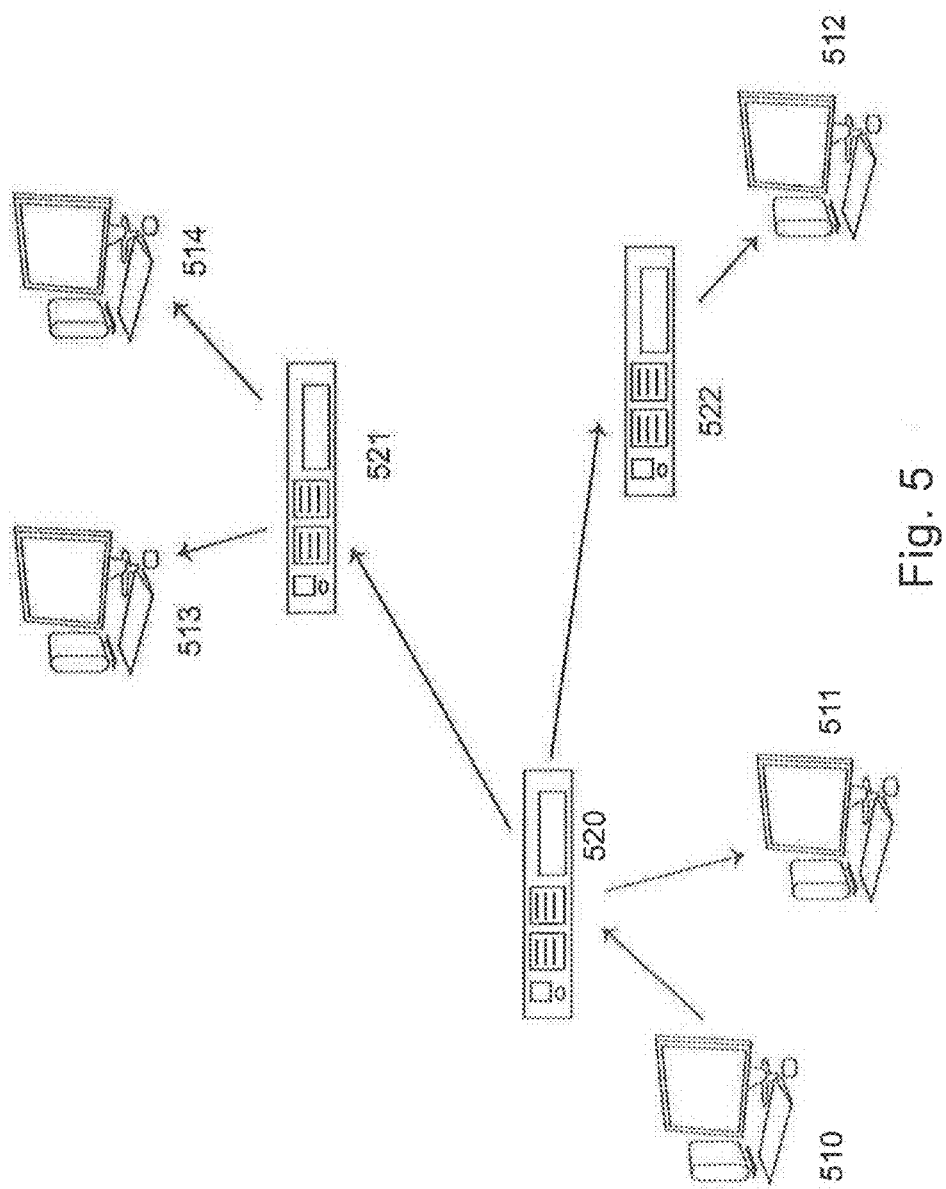
FIG. 5 illustrates an example data flow between a device and all other devices participating to the same video conferencing session in accordance with an aspect.

During a videoconference, each device may send to the server an audio/video stream and, if collaboration is active, a data stream as well. FIG. 5 illustrates the flow of data from a specific device 510 to the other devices in a videoconference. For example, server 520 may retransmit the received data signal from device 510 to each of the servers (e.g., 521, 522) to which at least one of the devices participating in the same session is connected (e.g., 511, 512, 513, 514) and each server 520, 521, 522 may then send the data signal to the participating devices (e.g., 511, 512, 513, 514) connected to the server (e.g., 520, 521, 522).

It is noted that the servers do not carry out any transcoding on the data flow, as typically happens in Multipoint Control Units (MCUs), the central communication hubs in traditional video conferencing systems, but may, for example, redirect traffic to participating devices.

An advantage may include considerable containment of the costs of the server, as it may not be necessary to have arrangements that include adequate computing power for decoding each received video signal input, the composition of a new video signal for each recipient being given by the union of the video signals of the other participants, and the encoding of the new video signal for transmission to the recipient. This approach may reduce the cost of each server's hardware, for example, as transcoding requires significant hardware resources.

In addition, another advantage may include minimizing the costs associated with band interconnection among servers because each signal may, for example, be sent only once to each server, regardless of how many devices are connected to each server for the same videoconference. Each device may receive from the server, in an independent manner, the various data streams from other participating devices.

Each stream may be identified at the level of network protocol, with a value pair of channel/sub-channel for each device with an audio channel, a video channel, and a data channel for collaboration. Each channel may be further divided into sub-channels that identify different versions of the same content. For example, an audio channel may be provided in the original language, such as English and a series of sub-channels of audio may be translated into different languages, such as Spanish, French, German, and Chinese. In addition, the video may have sub-channels characterized by different quality. These are just examples of the possible uses of the channel/sub-channel pair and are not exhaustive.

Thanks to the use of the channel/sub-channel pair, one or more or each device may have the ability to select among all the flows that the server has available to transmit, a portion of the flows to be transmitted, thereby saving download bandwidth.

The initial characteristics of the videoconference (e.g., an overall quality), may be selected by the user (host) who creates the meeting and may depend, in addition to the capabilities of his/her device, on the bandwidth that is allocated to the session. For example, the greater the allocable bandwidth, the higher the quality that may be obtainable for each device.

Each participating device involved in the videoconference may be queried to ensure as much as possible that the required quality is maintained, and that the program runs an initial verification of the characteristics of each device to determine any changes to be made.

Specifically, for example, it may be determined whether or not the required bandwidth is available for the given device, and then, on the basis of the bandwidth actually being used (which may be less than or equal to that required), the best possible combination of frame size/frame rate (among those supported by the camera of the device) may be determined and used to encode video.

Figure 6:
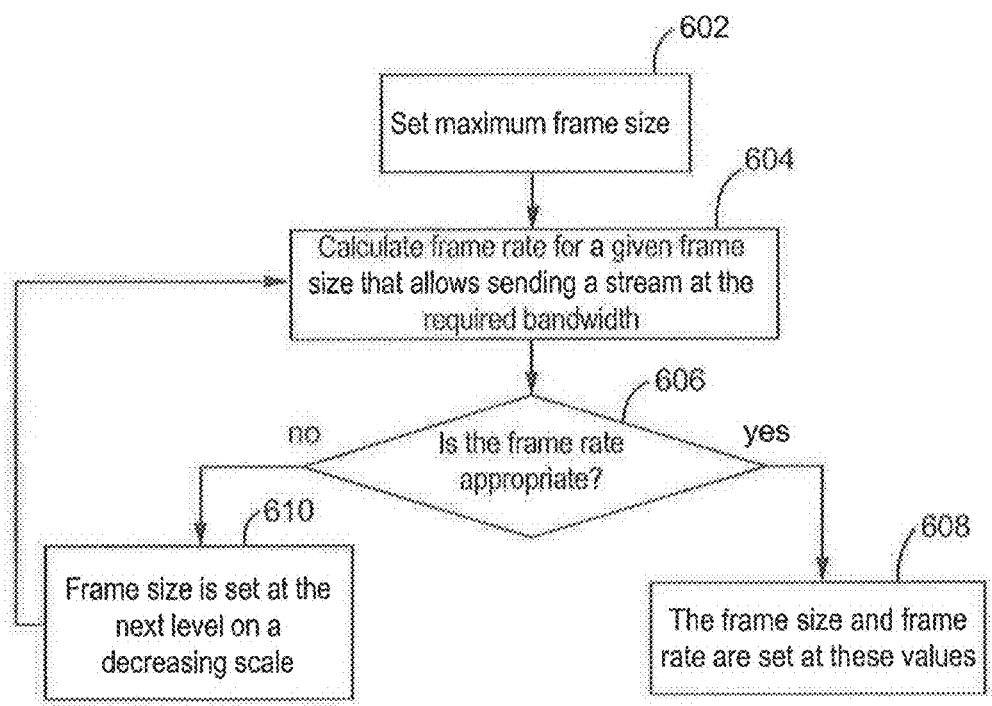
FIG. 6 illustrates an example method flow of determining a best frame size/frame rate combination for video encoding on a device in accordance with an aspect of the present invention.

FIG. 6 illustrates an example method flow in accordance with an aspect of the present invention. The method may include setting a maximum frame size for the video capturing device 602. For example, the system may determine a maximum frame size for the video capturing device and set the frame size. The choice of the best combination of frame size/frame rate may be a key factor in the video quality. Frame size (i.e., the size—or resolution—of every single video frame), and frame rate (i.e., how many video frames are created in a given time—the greater this number, the higher the fluidity of the video) may be key determinants of the output bit rate (i.e., the bandwidth used) by each device. Below a certain frame rate, the video may lose fluidity, and a lower resolution but a greater fluidity of movement may be preferable. The method may also include calculating a frame rate for a given frame size that allows transmission of a stream at a required bandwidth 604. For example, the system may determine the best resolution offered by the video capturing device (e.g., camcorder and capture card, webcam, network cam) and may determine the best frame rate possible given the bandwidth set for the meeting.

The method may include determining whether the frame rate is appropriate 606. If such a frame rate is greater than the minimum acceptable value, the method may include setting the frame size and frame rate to the determined values 608, and the process may end. If the frame rate is lower than the minimum acceptable value, the method may include setting a lower resolution and re-evaluating the frame rate used 610. In an aspect, the system may set the frame size at the next level on a decreasing scale.

The process may be continuously repeated until any of the following two conditions are met, for example: the process has set an appropriate frame rate, and none of the resolutions supported by the video capturing device meets the bandwidth limitation with adequate fluidity. In this case, the process uses the minimum resolution offered by the camera, with the lowest possible frame rate value.

Figure 7:
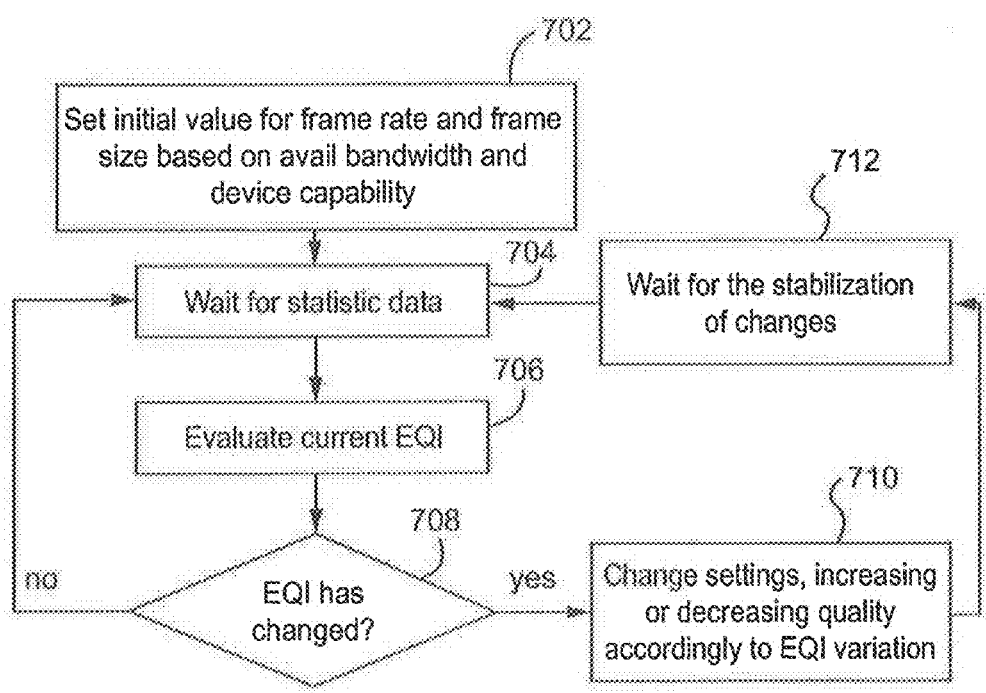
FIG. 7 illustrates an example method flow for determining the equivalent quality index (EQI) in accordance with an aspect of the present invention.

FIG. 7 illustrates a method flow for determining the equivalent quality index (EQI) in accordance with an aspect of the present invention. The method may include setting an initial value for frame rate and frame size based on available bandwidth and device capability 702. Once the initial parameters have been identified, the program may set the parameters and connect the device to the videoconferencing session. As shown in FIG. 7, during the session, the program may continuously monitor a variety of parameters relating to the device, as well as the performance of the overall videoconferencing session. These parameters are summarized in an "equivalent quality index" (EQI) that each device transmits to the program resident on the host device.

The method may include waiting for statistical data 704 and evaluating a current EQI 706. In an aspect, statistical data may include the parameters taken into consideration for the EQI, for example. The parameters taken into consideration may include (where applicable): overall CPU consumption; kernel CPU consumption; CPU consumption by the program; packet loss; audio jitter; video jitter; RTT to and from the server; upload bandwidth; and download bandwidth. These parameters may be device-specific values linked to a single device, or vectors, associated with the interaction of each device with the others participating in the videoconferencing session.

In particular, device-specific values may include CPU consumption, RTT, and bandwidth; vectors may include Packet Loss and jitter, since each device keeps track of packet loss, and audio/video jitter with all other devices participating in the session, for example.

The method may include determining whether the EQI has changed 708 and changing settings according to the EQI variation 710. In an aspect, the changes to the settings may include increasing or decreasing quality according to the EQI variation. For example, based on the EQI, each device may change its parameters to improve performance whenever necessary. In addition, the host device (which has a global view of the session's perceived quality) may change the general parameters of the videoconference, to which each participating device will immediately adapt.

The areas of intervention on which the program acts to control EQI may depend on which factor is causing a decline of the EQI. Such factors may include drop in upload bandwidth, for example. As several sub-channels may be sent by each device, for example, the first option in case of limited upload bandwidth may be to change the quality of each sub-channel sent.

Changes in video capturing settings may have an impact both on the upload bandwidth used, and on the consumption of device resources, as both may increase when frame rate and frame size go up. Given the heterogeneity of devices and networks, there may be cases where bandwidth does not impose any limit while the device's computing power does, or vice versa.

In particular, for example, when the available upload bandwidth declines for several seconds without recovering (for sporadic or temporary dips of short duration, even if significant in terms of amplitude, the mechanism of the asynchronous TCP socket allows the system to minimize the EQI's decline), the program may lower frame size and/or frame rate to stay within the changed bandwidth limits.

If the bandwidth reduction is drastic, the transmission of all video sub-channels may, for example, also be suspended and replaced by a static image of the user. Similarly, if the CPU consumption linked to the video encoding process is high, the program may lower frame size and/or frame rate.

The reduction of the frame size obviously may result in a degradation of the video quality received from all devices except the one sending it, causing a degradation of the overall quality of the session perceived by all participants. However, the reduction is likely to be minimal and is still preferable to an interruption of the videoconferencing session itself, provided the EQI is kept at acceptable levels. A reduction of the frame rate may be more difficult to perceive by users, given the static nature of many meetings.

In case of problems in download bandwidth, the device may switch from the highest quality sub-channel (the default option) to lower quality ones, or, for example, suspend video reception and replace the video reception with a static image.

Deselection of one or more video streams received, or switching from a video stream of high quality to that of a low quality, may be made possible by registering on the server which channels/sub channels for which the device is set or selected to receive. For example, when high-definition videoconferencing occurs between communication devices, even with adequate bandwidth, to which a device with low bandwidth is added. The low bandwidth device may tune to a low resolution sub-channel and still be able to participate without affecting the quality of other participants.

Of course, the quality of the audio-video received by the low bandwidth device may be lower than the quality of high definition devices, but these two "worlds" may be able to communicate at the best of their abilities.

Overall reduction of bandwidth for use in videoconferencing may be controlled by the host device, which may intervene when the host device determines or otherwise senses or receives information that, in general, there are quality problems related to the band used. For example, when the host device finds that the EQIs sent by several devices signal a widespread quality problem due to network congestion, the host may reduce the overall bandwidth of the meeting by sending a command to all other devices in the videoconferencing session. For some devices, this may lead to a change in the video encoding parameters.

The EQI monitoring may be continuous during each videoconferencing session. The method may further include waiting for the stabilization of changes to any parameter 712. For example, when the system changes any parameter on the basis of an unsatisfactory EQI, there may be a non-responsive period, during which further EQI signals are ignored in order to assess the impact of the changed parameters on EQI(s). If changes have not been made to the EQI, the method may return to 704 and wait for statistic data.

One variation of the described aspects may include monitoring EQI during other forms of communications, such as, but not limited to, cell phone calls, television over IP broadband, IP network control, and using the described aspects to maintain a level of quality assurance during the communications.

Figure 11:
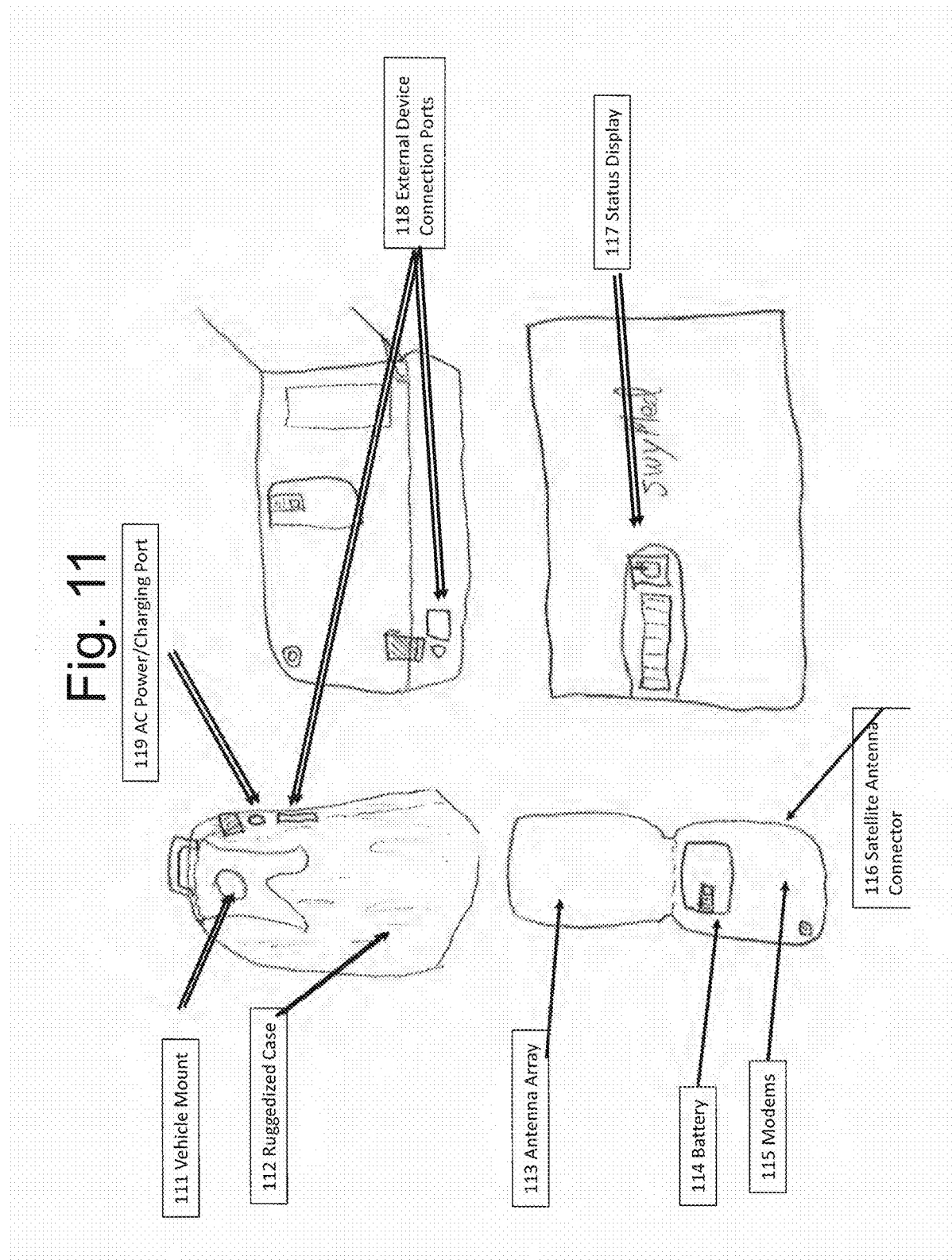
FIG. 11 illustrates an example prototype backpack in accordance with an aspect of the present invention.

In the event that a wired network is not available for videoconferencing and collaboration, a cellular, satellite or other wireless network may be utilized. Mobile communications equipment of sufficient capacity to enable video communications has traditionally been big, bulky and expensive. At a minimum, the size of a large suitcase. The described aspects have changed that expectation by designing a small backpack (100), slightly larger than a typical hiking daypack, as illustrated in FIG. 11. The small backpack (100) may contain a ruggedized case (112) to withstand extended field use under difficult conditions, any of a number of power supplies (such as battery (114), solar collector, AC plug (119)); communications devices (such as gateway modems for cellular or satellite internet) (115, 116), a multi-antenna array for connecting to cellular or satellite (113), hubs for physically connecting to peripheral devices for any number of computing devices such as tablet computers (118) (See, for example, FIG. 14), body cameras, video-enabled glasses and other wearable technologies. While the backpack (100) may be worn, the backpack (100) may also include a carry handle and vehicle mount so the backpack (100) may be secured when in a moving vehicle (e.g. ambulance).

The backpack (100) may meet the needs of mobile professionals, by providing a resilient network architecture and machine learning to enable predictive network switching to optimize the user experience.

Figure 10:
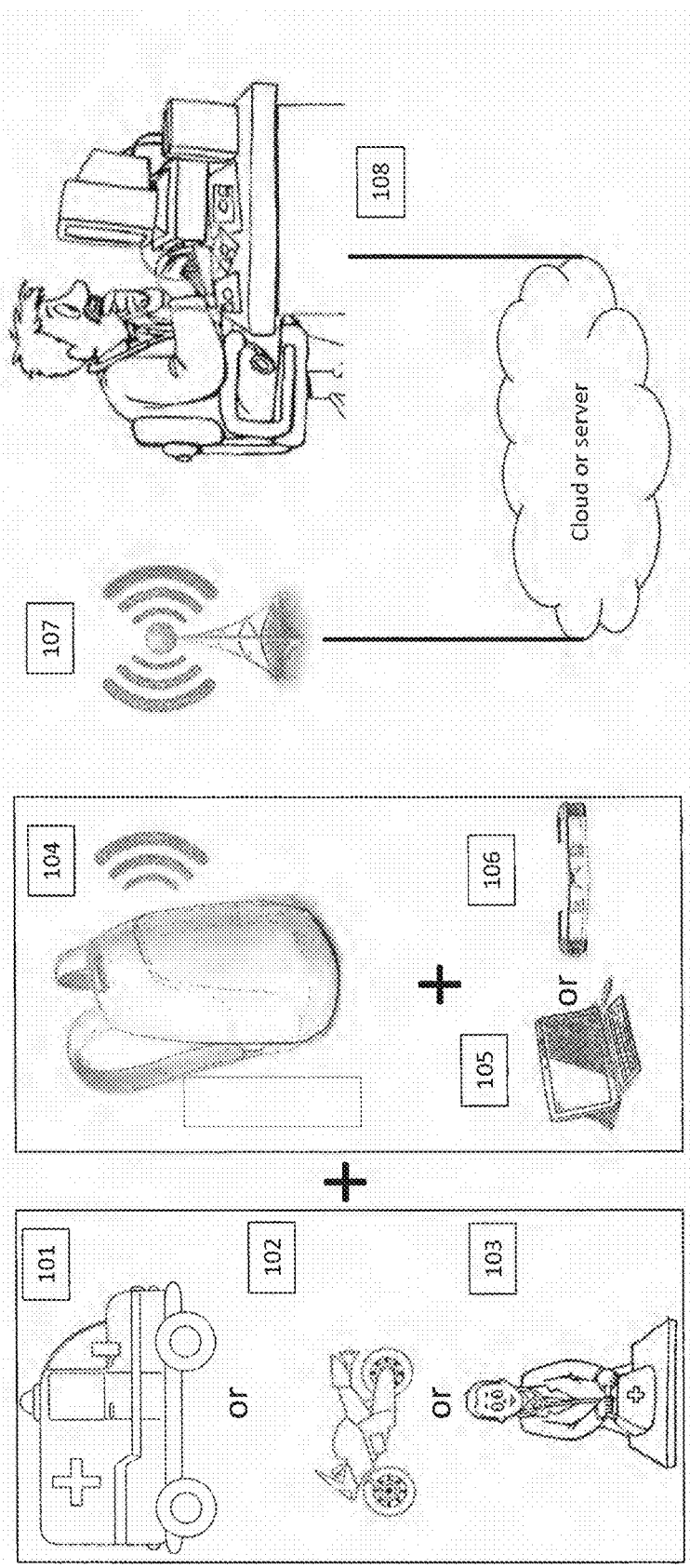
FIG. 10 illustrates the connection from a field professional to a medical center through the communication device in accordance with an aspect of the present invention.

One mobile professional population that may derive immediate benefit from the mobile communication technology are mobile healthcare workers seeking to connect over a secure network from multiple locations to physicians in hospitals or on call at home, as illustrated in FIG. 10. For example, mobile healthcare workers 103, such as EMTs and paramedics, often need support from a medical professional 108, such as physicians, when taking care of patients in the field. Currently physicians may provide support mostly by phone or radio but direct visual contact between physicians and patient could reduce stress for all parties and improve outcomes for patients while allowing hospitals to increase revenues and/or cut costs. The described aspects may include a mobile communications backpack (100) that may provide mobile healthcare workers (103) video communications (e.g., videoconference call and/or collaborations) with one or more remote devices of a medical professional (108) via a cellular network (107). In an aspect, the mobile communications backpack (100) may include a telemedicine backpack to be used by mobile healthcare workers. Healthcare is only one example, a similar approach may be used in other sectors whenever a subject matter expert needs to connect to a less skilled worker in the field and guide him/her in the execution of a complex task.

An example of the communications backpack (100) functionality, may include a vehicle (101, 102) or technician carrying the backpack (103). The backpack (100) may provide a broadband internet signal (104) which connects to a cellular tower (107) or a satellite (not pictured). A tablet computer (105), smart glasses (106), or any number of computing devices may connect to the broadband signal provided by the communications backpack (100) using, for example, the video collaboration software and connecting to the cloud server, as described elsewhere in this document. A medical professional in a remote location may use one or more remote devices (108) using the video collaboration software to engage in real-time or near real-time video dialogue to discuss medical conditions observed by the technician (103) to provide advice, assistance in diagnosis or information about appropriateness or availability of treatment at his/her facility.

Mobile communications may be inherently more prone to loss than fixed networks due to a number of technical factors which are well known in the field, as illustrated in FIG. 12. For example, an initiating location (121) may send data (122) to a cellular tower (123) or satellite (not pictured). Data received at the tower (124) or satellite may not be complete. From the tower/satellite, data is transmitted via internet technologies (125) to a server in a "cloud data center" (127). For example, data packets may be lost during transmission due to congestion at the tower (124), while other data packets may be lost during transmission, resulting in an even further degraded set of data packets being received by the server (126). The degraded set of data packets, when transmitted to the remote participant results in reduced quality audio and video.

Figure 13:
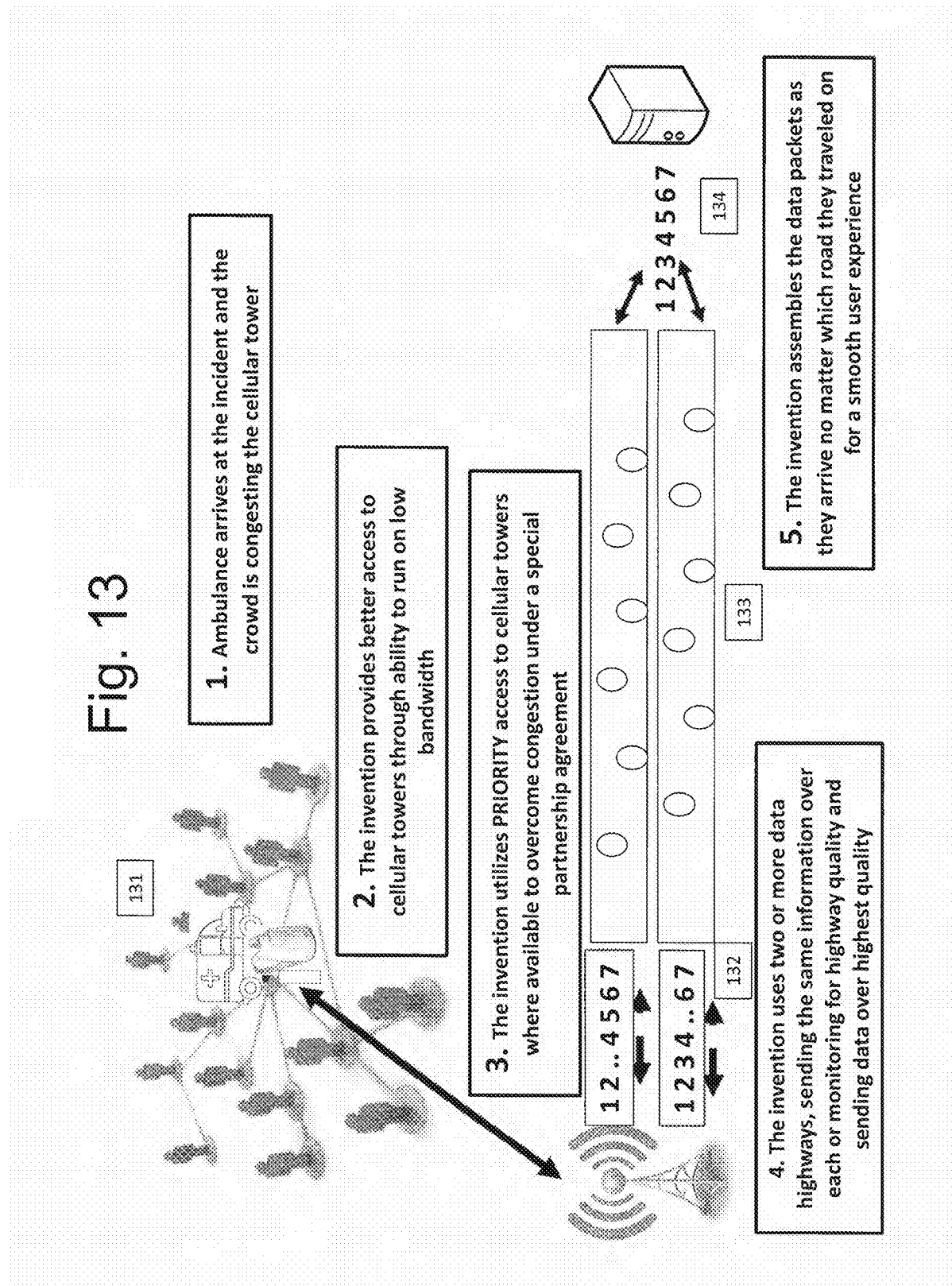
FIG. 13 illustrates an example solution to data loss over cellular data networks in accordance with an aspect of the present invention.

The described aspects provide a network approach that may consist of multiple data paths flowing from the initiating location (131), as illustrated in FIG. 13. The ability of the video collaboration software to perform over limited bandwidth may improve the likelihood that the video collaboration software may make a connection with a cellular tower or satellite. In addition, contractual relationships with carriers providing for network priority or separation of traffic from general consumer traffic may improve the likelihood of connection, particularly during surge events such as disasters or localized traffic disruptions. In an aspect, the stream of identical data packets may be sent by the software client over a single wireless or wired connection between one or more devices and the backpack (100) may be transmitted over at least two unique wide-area network connections (e.g., cellular networks, satellite networks, WiFi, radio, or any combination of transmission mechanisms) to multiple addresses of the server software, thus, improving the likelihood that a complete set of data packets may be received at the server (134). Despite losses in data received at the tower (132) and data losses in network transmission (133), the combination of data streams at the server based on packet-level identification (134) and first-in first-out packet selection may provide a complete data stream from the initiating site (131), improving quality of experience for all participants without requiring multiple network cards on devices at the initiating location and that may not be available on the devices, such as smart glasses or mobile devices.

Figure 14:
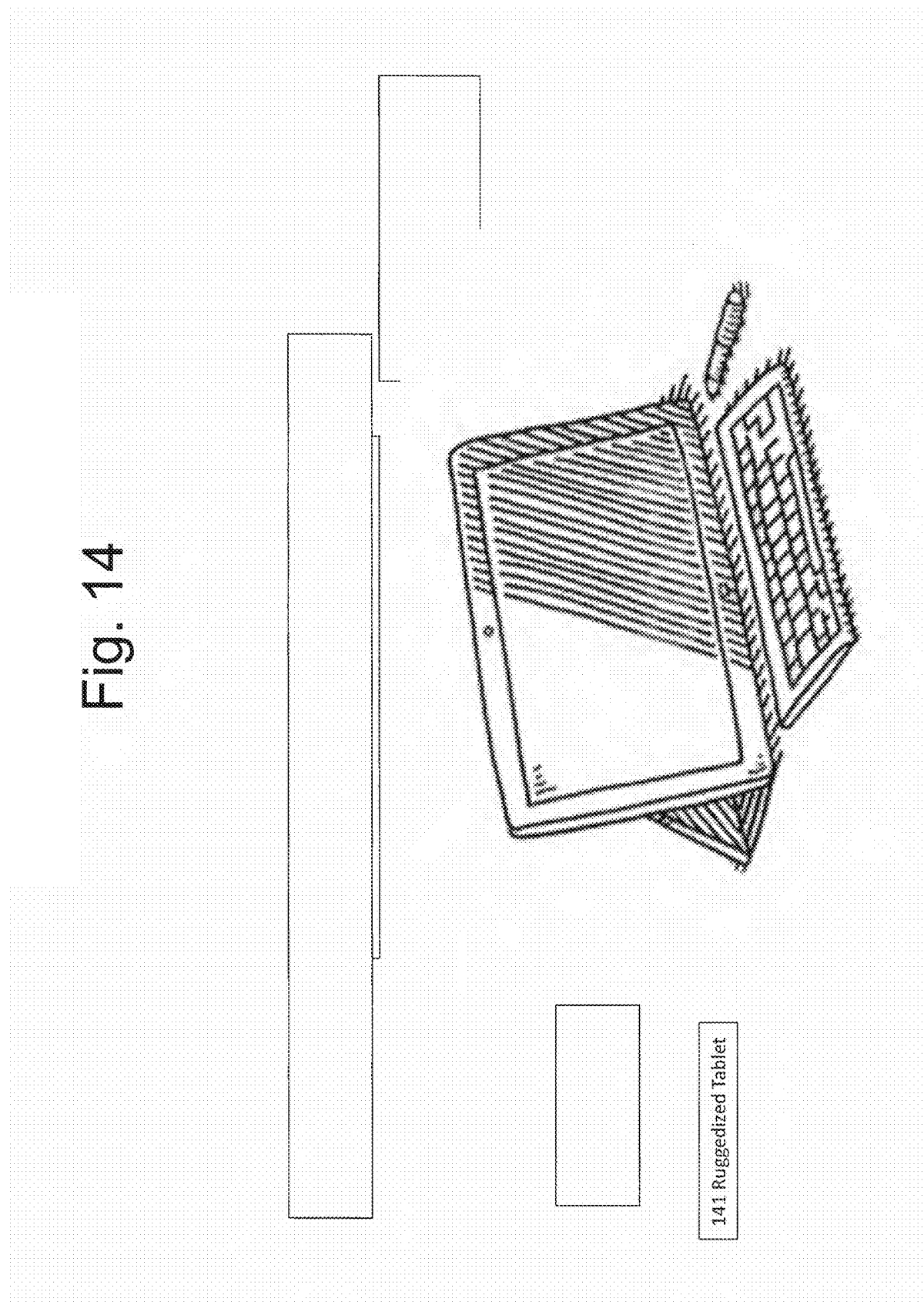
FIG. 14 illustrates an example tablet computer used by a mobile professional in accordance with an aspect of the present invention.

FIG. 14 illustrates an example of a ruggedized tablet, one of a number of possible computing devices that may connect to the communications backpack (100). The tablet may contain the video collaboration software and may provide the display, microphone, speaker and camera to capture images and sound at the initiating site for transmission through the communications backpack. USB, Bluetooth or other connection technologies can be used to attach additional devices including, but not limited to, Food and Drug Administration (FDA) registered bio-medical devices, specialty cameras and sound systems, or to connect to an external system such as a vehicle, clean suit, space suit, or diving suit.

Figure 16:
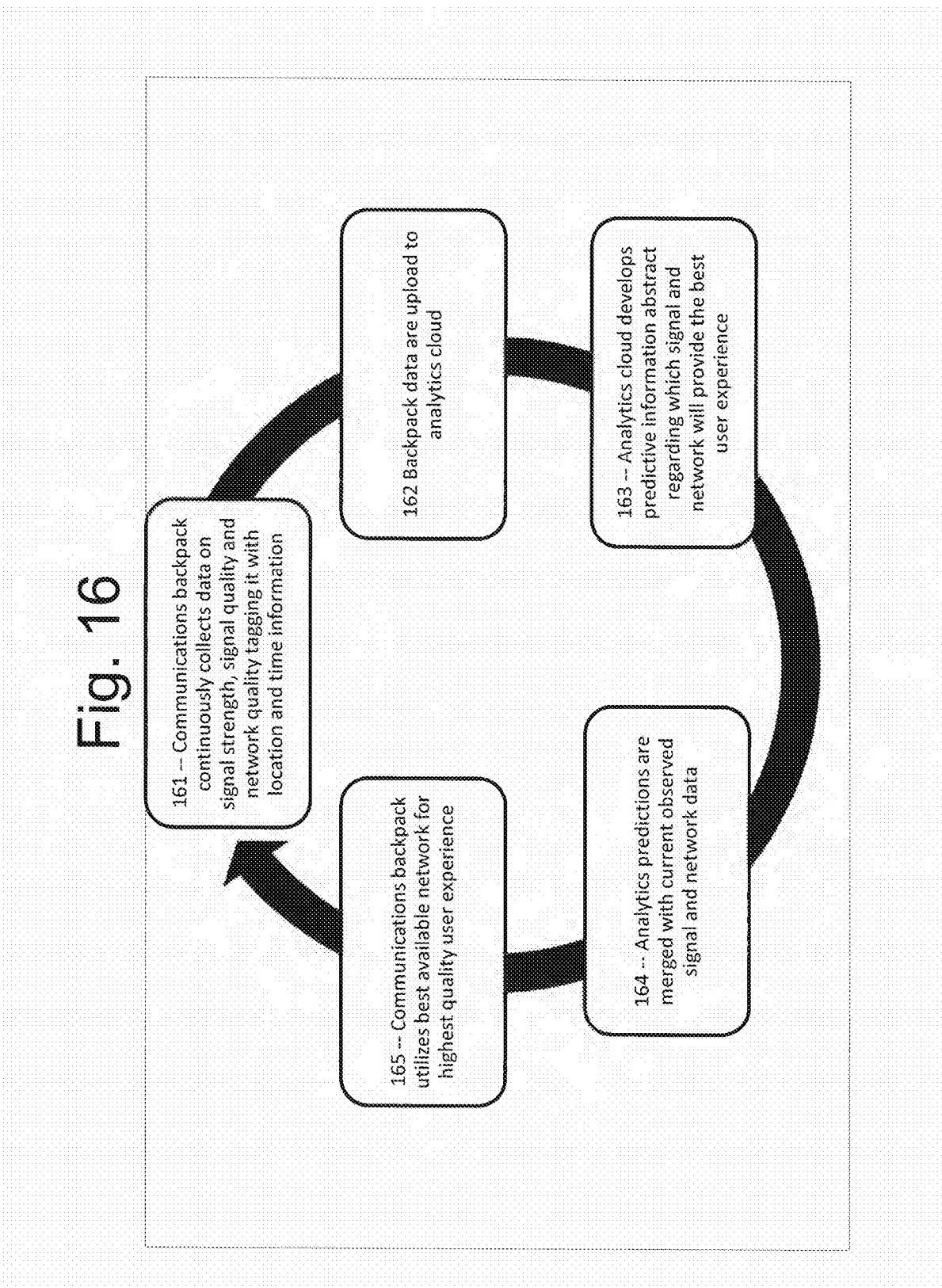
FIG. 16 illustrates an example method flow in accordance with an aspect of the present invention.

An example method flow for machine learning and predictive switching technology for best possible user experience is illustrated in FIG. 16. As the communications backpack moves over the course of daily use, network monitoring software may collect data on signal strength, signal quality, and network performance at points in time, over time periods. The collected data may be tagged by location based on Global Positioning System (GPS) information available to the communications device (161). In the course of a single day of operations, the communications backpack (100) may amass tens of thousands of readings, relating to the availability and quality of signal/network across multiple possible networks. This dataset may continually update as the communications backpack travels and operates. In addition, the GPS-tagged dataset may be uploaded to an analytics cloud (162) and may be continually analyzed to extract predictions for the "best available" network for a given location, time of day, day or week, and other criteria which may change over time with continued review of the data (163). The continuously updating predictions of best available network based on dynamic network monitoring data and historical experience may be merged in the communications backpack (164). The combination of the current readings observed and the historical experience may enable the video collaboration software to become increasingly effective in switching to the networks that are expected to have the best performance for a given time and location (165). By switching traffic to the best performing network before disruptions are encountered, the user experience of all participants may be further enhanced and cost may be reduced as redundant transmission may be limited to the two best performing networks in any given area.

Figure 15:
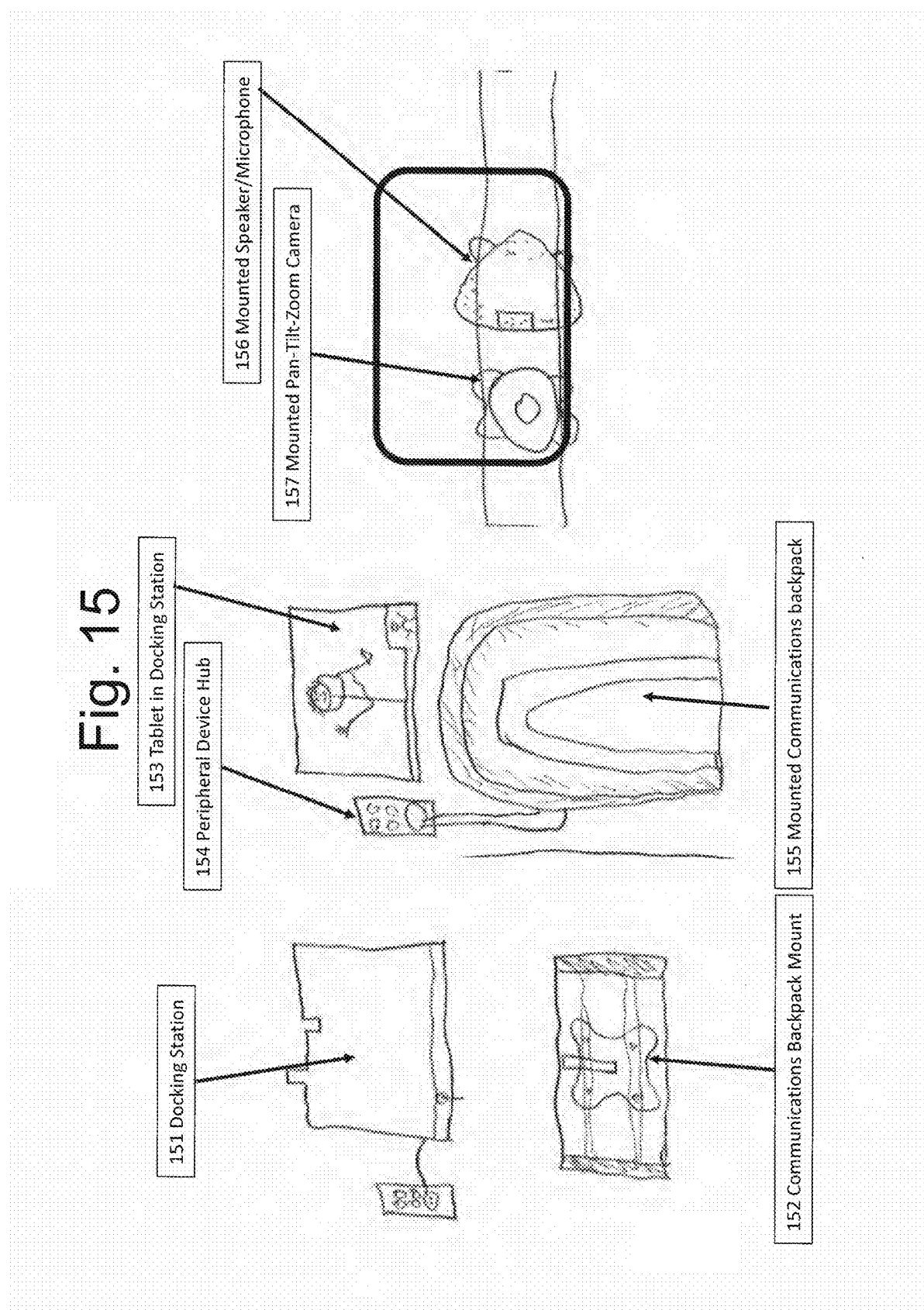
FIG. 15 illustrates an example mounting system for mounting a backpack and tablet to a vehicle and providing clear sound and remote control camera movement in accordance with an aspect of the present invention.

In an implementation, the communications backpack (100) may be installed in a mobile vehicle. For installation into a mobile vehicle (e.g., an ambulance), additional issues including crash safety, road noise, and hands free operation may be considered to maintain the quality of user experience. The described aspects may use industry leading technologies to address each of these aspects. For example, a mounting system designed for mobile healthcare may connect the backpack to the vehicle, a noise cancelling speaker/microphone may remove background noise while allowing free communication between occupants/patients and remote doctors, a pan-tilt-zoom camera mounted in the vehicle may augment the camera on the computer used for the video call. In addition, the communications backpack (100) can be attached to a vehicle using a system of certified and crash rated mounts to ensure the safety of use under moving conditions. FIG. 15 illustrates a sample docking station for a tablet (151) and mount for the communications backpack (152). The tablet mounted in the docking station (153) and communications backpack mounted (155) can be attached to power for charging or external devices through Bluetooth, WiFi, USB, Ethernet or other communications technologies (154). Examples include a high quality echo cancelling speaker microphone (156) and a Pan-tilt-zoom camera (157) which can also be mounted in certified, crash-tested mounting brackets.

Figure 17:
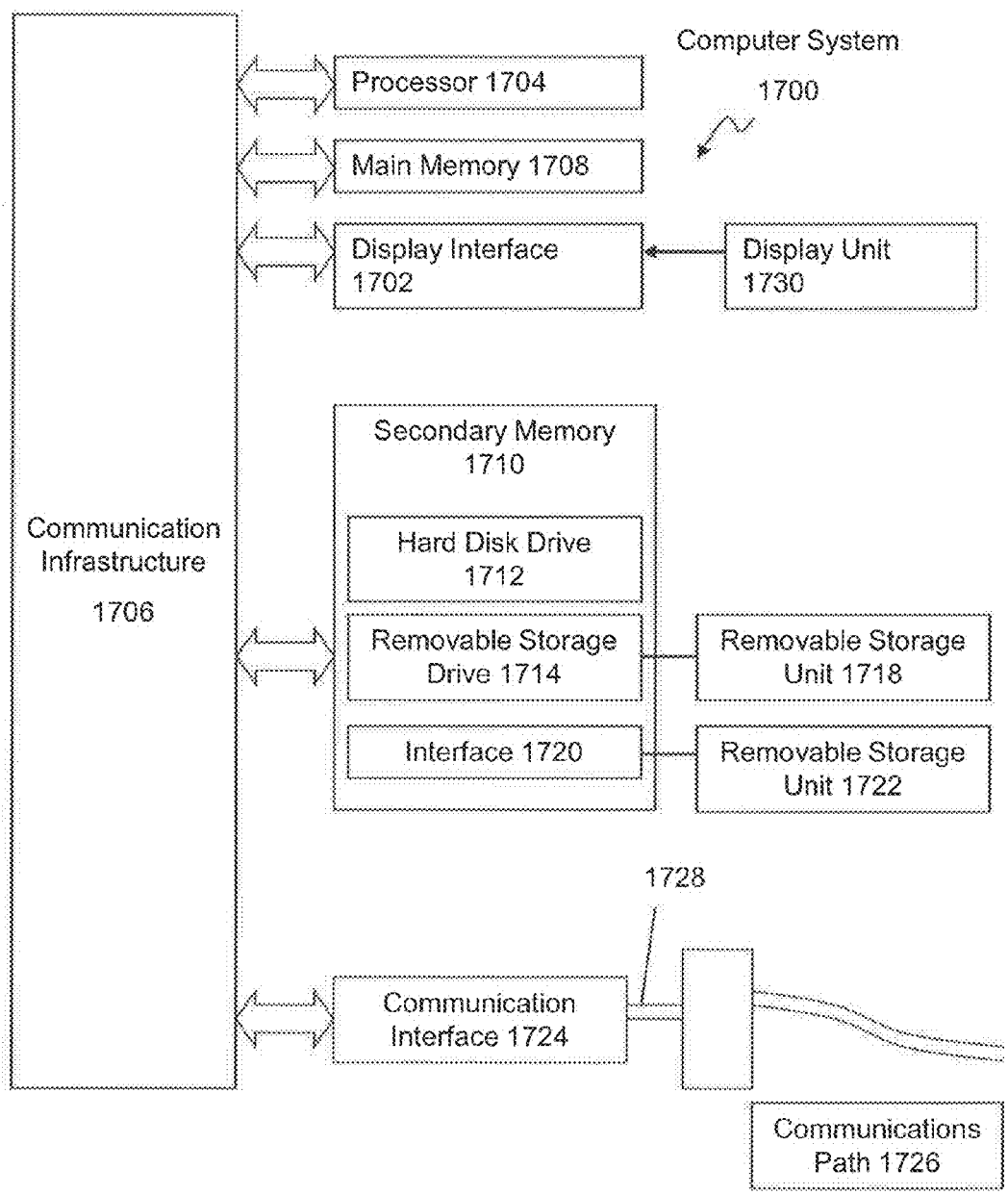
FIG. 17 illustrates various features of an example computer system for use in conjunction with aspects of the present invention.

Aspects of the present invention may be implemented using hardware, software, or a combination thereof and may be implemented in one or more computing systems or other processing systems. In an aspect of the present invention, features are directed toward one or more computing systems capable of carrying out the functionality described herein. An example of such a computer system 1700 is shown in FIG. 17.

Computer system 1700 includes one or more processors, such as processor 1704. The processor 1704 is connected to a communication infrastructure 1706 (e.g., a communications bus, cross-over bar, or network). Various software aspects are described in terms of this exemplary computer system. After reading this description, it will become apparent to a person skilled in the relevant art(s) how to implement aspects of the invention using other computer systems and/or architectures.

Computer system 1700 can include a display interface 1702 that forwards graphics, text, and other data from the communication infrastructure 1706 (or from a frame buffer not shown) for display on a display unit 1730. Computer system 1700 also includes a main memory 1708, preferably random access memory (RAM), and may also include a secondary memory 1710. The secondary memory 1710 may include, for example, a hard disk drive 1712 and/or a removable storage drive 1714, representing a floppy disk drive, a magnetic tape drive, an optical disk drive, a universal serial bus (USB) flash drive, etc. The removable storage drive 1714 reads from and/or writes to a removable storage unit 1718 in a well-known manner. Removable storage unit 1718 represents a floppy disk, magnetic tape, optical disk, USB flash drive etc., which is read by and written to removable storage drive 1714. As will be appreciated, the removable storage unit 1718 includes a computer usable storage medium having stored therein computer software and/or data.

Alternative aspects of the present invention may include secondary memory 1710 and may include other similar devices for allowing computer programs or other instructions to be loaded into computer system 1700. Such devices may include, for example, a removable storage unit 1722 and an interface 1720. Examples of such may include a program cartridge and cartridge interface (such as that found in video game devices), a removable memory chip (such as an erasable programmable read only memory (EPROM), or programmable read only memory (PROM)) and associated socket, and other removable storage units 1722 and interfaces 1720, which allow software and data to be transferred from the removable storage unit 1722 to computer system 1700.

Computer system 1700 may also include a communications interface 1724. Communications interface 1724 allows software and data to be transferred between computer system 1700 and external devices. Examples of communications interface 1724 may include a modem, a network interface (such as an Ethernet card), a communications port, a Personal Computer Memory Card International Association (PCMCIA) slot and card, etc. Software and data transferred via communications interface 1724 are in the form of signals 1728, which may be electronic, electromagnetic, optical or other signals capable of being received by communications interface 1724. These signals 1728 are provided to communications interface 1724 via a communications path (e.g., channel) 1726. This path 1726 carries signals 1728 and may be implemented using wire or cable, fiber optics, a telephone line, a cellular link, a radio frequency (RF) link and/or other communications channels. In this document, the terms "computer program medium" and "computer usable medium" are used to refer generally to media such as a removable storage drive 1714, a hard disk installed in hard disk drive 1712, and signals 1728. These computer program products provide software to the computer system 1700. Aspects of the invention are directed to such computer program products.

Computer programs (also referred to as computer control logic) are stored in main memory 1708 and/or secondary memory 1710. Computer programs may also be received via communications interface 1724. Such computer programs, when executed, enable the computer system 1700 to perform the features in accordance with aspects of the present invention, as discussed herein. In particular, the computer programs, when executed, enable the processor 1704 to perform the features in accordance with aspects of the present invention. Accordingly, such computer programs represent controllers of the computer system 1700.

In an aspect of the present invention that is implemented using software, the software may be stored in a computer program product and loaded into computer system 1700 using removable storage drive 1714, hard drive 1712, or communications interface 1720. The control logic (software), when executed by the processor 1704, causes the processor 1704 to perform the functions described herein. In another aspect of the present invention, the system is implemented primarily in hardware using, for example, hardware components, such as application specific integrated circuits (ASICs). Implementation of the hardware state machine so as to perform the functions described herein will be apparent to persons skilled in the relevant art(s).

In yet another aspect of the present invention, features thereof is implemented using a combination of both hardware and software.

Figure 18:
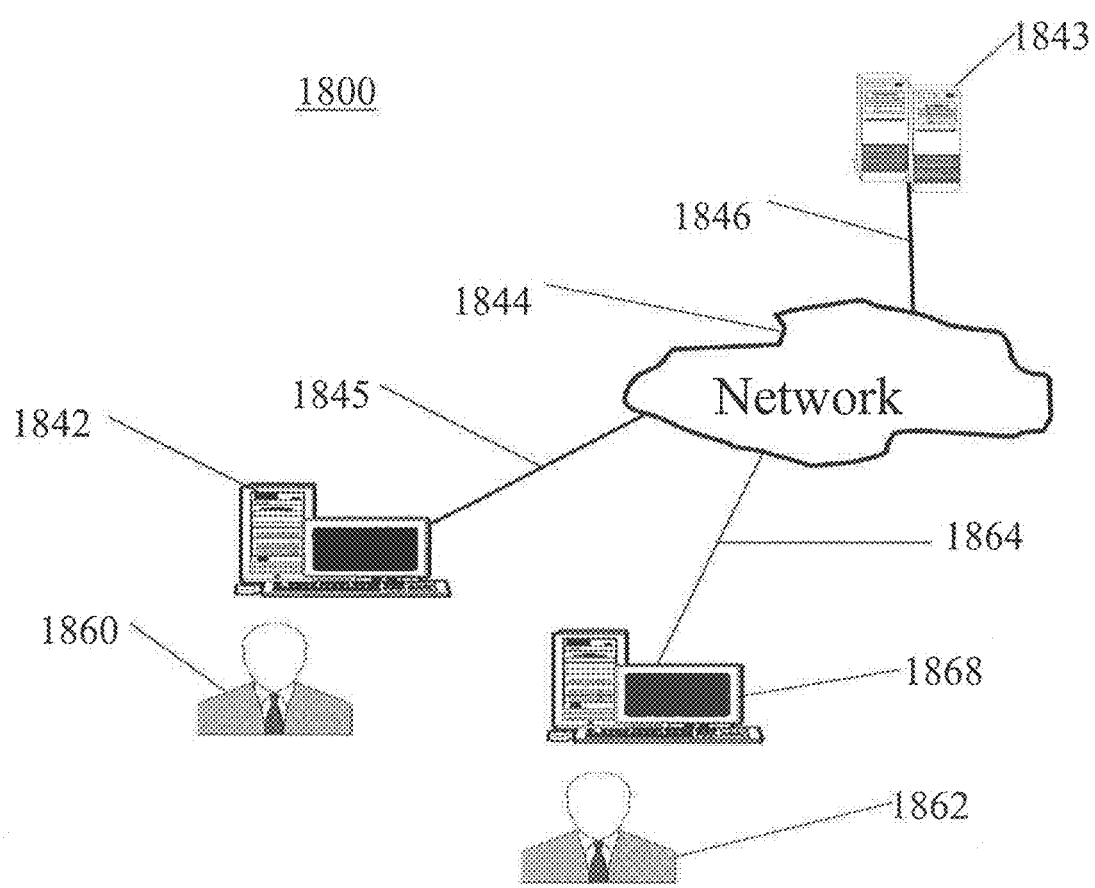
FIG. 18 illustrates an exemplary system diagram of various hardware components and other features for use in accordance with aspects of the present invention.

FIG. 18 shows a communication system 1800 usable in accordance with aspects of the present invention. The communication system 1800 includes one or more accessors 1860, 1862 (also referred to interchangeably herein as one or more "users") and one or more terminals 1842, 1868. In one aspect of the present invention, data for use is, for example, input and/or accessed by accessors 1860, 1862 via terminals 1842, 1868, such as personal computers (PCs), minicomputers, mainframe computers, microcomputers, telephonic devices, or wireless devices, such as personal digital assistants ("PDAs") or a hand-held wireless devices coupled to a server 1843, such as a PC, minicomputer, mainframe computer, microcomputer, or other device having a processor and a repository for data and/or connection to a repository for data, via, for example, a network 1844, such as the Internet or an intranet, and couplings 1845, 1846, 1864. The couplings 1845, 1846, 1864 include, for example, wired, wireless, or fiberoptic links.

While aspects of the present invention have been described in connection with examples thereof, it will be understood by those skilled in the art that variations and modifications of the aspects of the present invention described above may be made without departing from the scope hereof. Other aspects will be apparent to those skilled in the art from a consideration of the specification or from a practice in accordance with aspects of the invention disclosed herein.

The invention claimed is:

1. A method for mobile videoconferencing, comprising:
establishing a videoconference or collaboration call between at least one communications backpack and at least one remote device via a wireless network;
transmitting identical data packets for the videoconference or collaboration call over at least two network connections of the wireless network;
combining the received data packets into a single complete data stream using the received data packets from any of the at least two network connections assembled in order based on packet-level identification for presentations to users in the videoconference or collaboration call;
receiving network data from the at least one communications backpack;
storing the received network data;
tagging the received network data with a location and a time;
continuously monitoring a plurality of network connections of the networks during the videoconference or collaboration call to determine current network conditions; and
selecting a network connection to transmit the data packets for the videoconference or collaboration call based on the current network conditions.

2. The method of claim 1, further comprising:
determining a predicted network condition for a specific location and a specific time based on the stored network data for the specific location and the specific time.

3. The method of claim 2, wherein selecting the network connection of the wireless network to transmit the data packets further comprises using the predicted network condition and the current network conditions.

4. The method of claim 2, further comprising:
selecting the network connection of the available networks to transmit the data packets for the videoconference or collaboration call based on the predicted network conditions.

5. The method of claim 1, wherein the communications backpack is a lightweight portable backpack.

6. The method of claim 1, wherein the communications backpack is secured to a vehicle.

7. The method of claim 1, wherein the communications backpack communicates with external components to enhance user experience.

8. The method of claim 1, wherein the users are healthcare workers, or other expert professionals advising less highly skilled field workers using videoconferencing and collaboration software.

9. A system for mobile videoconferencing or collaboration, comprising:
a platform operable by a processor to:
establish a videoconference or collaboration call between at least one communications backpack and at least one remote device via a wireless network;
transmit identical data packets for the videoconference or collaboration call over at least two network connections of the wireless network;
combine the received data packets into a single complete data stream using the received data packets from any of the at least two network connections assembled in order based on packet-level identification for presentations to users in the videoconference or collaboration call;
receive network data from the at least one communications backpack;
store the received network data;
tag the received network data with a location and a time;
continuously monitor a plurality of network connections of the wireless network during the videoconference or collaboration call to determine current network conditions; and
select a network connection of the wireless network to transmit the data packets for the videoconference or collaboration call based on the current network conditions.

10. The system of claim 8, wherein the platform is further operable to determine a predicted network condition for a specific location and a specific time based on the stored network data for the specific location and the specific time.

11. The system of claim 10, wherein the platform is further operable to select the network connection of the wireless network to transmit the data packets using the predicted network condition and the current network conditions.

12. The system of claim 10, wherein the platform is further operable to select the network connection of the wireless network to transmit the data packets for the videoconference or collaboration call based on the predicted network conditions.

13. The system of claim 8, wherein the communications backpack is a lightweight portable backpack.

14. The system of claim 8, wherein the communications backpack is secured to a vehicle.

15. The system of claim 8, wherein the communications backpack communicates with external components to enhance user experience.

16. The system of claim 8, wherein the users are healthcare workers, or other expert professionals advising less highly skilled field workers using videoconferencing and collaboration software.

17. The system of claim 8, wherein the wireless network includes one or more of a cellular network, a satellite network, and a radio network.

18. A computer program product, comprising:
a computer-readable medium comprising:
at least one instruction for causing a computer to establish a videoconference or collaboration call between at least one communications backpack and at least one remote device via a wireless network;
at least one instruction for causing the computer to transmit identical data packets for the videoconference or collaboration call over at least two network connections of the wireless network;
at least one instruction for causing the computer to combine the received data packets into a single complete data stream using the received data packets from any of the at least two network connections assembled in order based on packet level identification for presentations to users in the videoconference or collaboration call;
at least one instruction for causing the computer to receive network data from the at least one communications backpack;
at least one instruction for causing the computer to store the received network data;
at least one instruction for causing the computer to tap the received network data with a location and a time;
at least one instruction for causing the computer to continuously monitor a plurality of network connections of the wireless network during the videoconference or collaboration call to determine current network conditions; and at least one instruction for causing the computer to select a network connection of the wireless network to transmit the data packets for the videoconference or collaboration call based on the current network conditions.

\* \* \* \* \*